US00PP12902P2

(12) United States Plant Patent

Olesen et al.

(10) Patent No.: US PP12,902 P2

(45) Date of Patent: Sep. 3, 2002

(54) FLORIBUNDA ROSE PLANT NAMED 'POULRIBER'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/273,169

(22) Filed: Mar. 19, 1999

(51) Int. Cl.[7] ..... A01H 5/00

(52) U.S. Cl. ..... Plt./148

(58) Field of Search ..... Plt./147, 148, 149

(56) References Cited

U.S. PATENT DOCUMENTS

PP6,713 P * 4/1989 McGredy, IV ..... Plt./148

OTHER PUBLICATIONS

Copy of PL PBR ROA0059 filed Mar. 27, 1998 and Grant #01143 dated Feb. 24, 2000.*

Copy of QZ PBR 970138, filed Jan. 27, 1997 and EU3217 dated Jul. 20, 1998.*

UPOV–ROM, 2000/04, Plant Variety Database, GTI JOUVE Retrieval Software, 2 citations for 'POULriber'.*

* cited by examiner

*Primary Examiner*—Howard J. Locker

(57) ABSTRACT

A new garden rose plant which has abundant, salmon pink-colored flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed, non-patented seedling and 'MACrexy' (U.S. Plant Pat. No. 6,713). The two parents were crossed and the resulting seeds were planted in a controlled environment. The new variety is named 'POULriber'.

The new rose may be distinguished from its seed parent, an unnamed seedling, by the following combination of characteristics:

1. The seed parent is a miniature rose, and 'POULriber'is a Floribunda;

2. The blooms of the seed parent are pink; whereas, 'POULriber' has salmon pink-colored blooms;

3. The foliage of the seed parent is much smaller than 'POULriber'.

The new variety may be distinguished from its pollen parent, 'MACrexy', by the following combination of characteristics:

1. The color of the blooms of the pollen parent are medium pink; 'POULriber' has salmon pink-colored blooms.

2. The pollen parent has 40 petals per bloom, whereas 'POULriber' has 18–22 petals per bloom.

The objective of the hybridization of this rose variety for garden use was to create a new and distinct variety with unique qualities, such as:

1. Uniform and abundant flowers;

2. Vigorous, compact growth;

3. Continuous flowering during the growing season.

4. Disease resistance.

This combination of qualities is not present in previously available commercial cultivars of this type and distinguishes 'POULriber' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULriber' was selected in the Spring 1989 by the inventors as a single plant from the progeny of the aforementioned hybridization.

Asexual propagation of 'POULriber' by traditional budding was first done by L. Pernille and Mogens N. Olesen in August, 1989, in their nursery in Fredensborg, Denmark. This initial and other subsequent propagations conducted in controlled environments have demonstrated that the characteristics of 'POULriber' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULriber'. Specifically illustrated in SHEET 1:

1. Stem of the plant showing branching and the attachment of leaves, buds, and peduncles;

2. Flower bud, partially opened bud, and open bloom;

3. Flower petals, detached,

4. Sepals, receptacle, and pedicel;

5. A bare stem;

6. Leaves.

DETAILED DESCRIPTION OF THE VARIETY

The following is a description of 'POULriber', as observed in its outdoor growth in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULander', a Floribunda rose variety from the same inventors described and illustrated in U.S. Plant Pat. No. 6,265 and issued on Aug. 30, 1988 are compared to 'POULriber' in Chart 1.

CHART 1

| | 'POULriber' | 'POULander' |
|---|---|---|
| Size of open flower. | 65–75 mm. | 60–80 mm. |
| Petalage. | Double, 18–22 petals. | Double, 20 petals. |
| General tonality of flower. | Red Group 40C-41B. | Red Group 46B-C. |

Parents:

*Seed parent.*—Unnamed seedling.

*Pollen parent.*—'Macrexy'.

Classification:

*Botanical.*—*Rosa hybrida.*

*Commercial.*—Floribunda.

FLOWER AND FLOWER BUD

Blooming habit: Continuous.

Flower bud:

*Size.*—Upon opening, 35 mm–40 mm in length from base of recepticle to end of bud.

*Bud form.*—Pointed ovoid becoming more blunt as it matures.

*Bud color.*—As sepals unfold, Red Group 40A to 42B. Red Group 40A to 42B at ¼ opening.

*Sepals.*—Yellow-Green Group 146A. Weak foliaceous appendages. Innermost surfaces of sepals moderately pubescent. Stipitate glands are present in limited quantities on margins of some sepals.

*Receptacle.*—Surface: Smooth. Shape: Broadly funnel shaped. Size: Medium, 5 mm (h)×7 mm (w). Color: Yellow-Green Group 144B. Many with intonations of Greyed-Purple Group 183B.

*Peduncle.*—Surface: With abundant stipitate glands. Length: 45–55 mm average length. Color: Yellow-Green Group 144B, with intonations of Greyed-Purple Group 183B. Strength: Upright.

*Borne.*—Singular to multiple buds per stem, typically with 2–-4 buds per flowering stem.

Flower bloom:

*Fragrance.*—Little or no fragrance.

*Duration.*—Not observed as a cut flower. The blooms have a duration on the plant of approximately 7 to 9 days. Petals fall cleanly away from plant.

*Size.*—Average flower diameter is 65–75 mm when open.

*Form.*—Shape of flower when viewed from the side: Upon opening, upper part: Convex. Upon opening, lower part: Flattened convex. Open flower, upper part: Flat. Open flower, lower part: Flattened convex.

*Petalage.*—Double, with a range of 18–22 petals under normal conditions with 4–6 petaloids.

Color:

*Upon opening, petals.*—Upper surface: Innermost petals are Red Group 48A–C. Outermost petals are Red Group 48A at margin, fading on gradient into Red Group 49D at petal base. Lower Surface: Innermost petals are Red Group 48A–C. Outermost petals are Red Group 48A at margin, fading on gradient into Red Group 49D near petal base.

*Upon opening, basal petal spots.*—Outer Side: Green-Yellow Group 1C. Inner Side: Green-Yellow Group 1B and Yellow Group 2B.

*After opening, petals.*—Upper surface: Innermost petals are Red Group 48A–C. Outermost petals are Red Group 48A at margin, fading on gradient into Red Group 49D at petal base. Lower Surface: Innermost petals are Red Group 48A–C. Outermost petals are Red Group 48A at margin, fading on gradient into Red Group 49D near petal base.

*After opening, basal petal spots.*—Outer Side: Green-Yellow Group 1D. Inner Side: Green-Yellow Group 1D.

General tonality: On open flower, Red Group 40C–41B. No change in the general tonality at the end of the $4^{th}$ day. Afterwards, general tonality is Red Group 40D–41C.

Petals:

*Petal reflex.*—Petals flat or cupped inwards slightly.

*Petal edge.*—Uniform with small point or indentation in the center of margin.

*Shape.*—Broadly deltoid and in some cases ovoid.

*Petaloids.*—Typically 4–6 per flower.

*Texture.*—Thick.

*Arrangement.*—Informal.

Reproductive organs:

*Pollen.*—Color: Yellow-Orange Group 14C. Quantity: Abundant.

*Anthers.*—Size: Medium. Color: Immature: Yellow-Orange Group 12D. Mature: Greyed-Yellow Group 162D and Brown Group 200D. Quantity: Abundant.

*Filaments.*—Color: Yellow Group 1B.

*Stigmas.*—Slightly superior in location to anthers. Color: Yellow-Green Group 145D.

*Styles.*—Color: Green-White Group 157C with some styles having light intonations of Red-Purple Group 57C.

*Hips.*—None observed.

PLANT

Plant growth: Vigorous, upright to bushy. When grown as a budded field grown plant on *Rosa multiflora* understock the average height of the plant is 80 cm and the average width is 60 cm.

Stems:

*Color.*—Young wood: Green Group 137C. Older wood: Yellow-Green Group 146B–146C to Yellow Green Group 144B.

*Thorns.*—Incidence: Moderately thorny. Size: Variable, Average length: 5 mm–6 mm, some 8 mm long. Color: Yellow-Green Group 153C–Greyed-Orange Group 173C. Shape: Concave, with larger thorns exhibiting a slight downward curve.

*Surface.*—Young wood: Smooth. Older wood: Smooth.

*Length.*—From 50 to 70 cm.

Plant foliage: Normal number of leaflets on leaves in middle of the stem: 5 leaflets.

*Leaf size.*—Medium, 100–110 mm (l)×60–70 mm (w).

*Quantity.*—Average.

*Color.*—Upper Leaf Surface: Green Group 137A. Lower Leaf Surface: Green Group 137D–Yellow-Green Group 147C. Juvenile foliage: Upper surface:

Yellow Green Group 152C. Lower surface: Yellow-Green Group 152C. Anthocyanin: Found in all areas of juvenile leaflet except on the interior of the upper surface of the leaflet. Color is Greyed-Red Group 179A and Greyed-Red Group 181A.

Plant leaves and leaflets:

*Stipules.*—Size: 14 mm–16 mm average. Color: Yellow-Green Group 143B. Stipitate glands: Located on margins.

*Petiole.*—*Length*: 25 mm–35 mm. Color: Green Group 137B–137C. Underneath: Smooth, with 1–2 small prickles and a few stipitate glands. Margins: With limited numbers of stipitate glands.

*Rachis.*—Color: Green Group 137B–137C. Underneath: Smooth, with limited numbers of small prickles. Margins: Have limited number of stipitate glands.

*Leaflet.*—Edge: Serrated. Shape: Ovate to round. Texture: Moderately glossy, thick.

Disease resistance: Above average resistance to mildew, black spot, and Botrytis under normal growing conditions in Jackson County, Oreg.

Cold hardiness: 'Poulriber' has been found to be cold hardy in Fredensborg, Denmark and in Jackson County, Oreg.

We claim:

1. A new and distinct variety of rose plant of the Floribunda class, substantially as herein illustrated and described as a distinct and novel rose variety due to its abundant, salmon pink-colored flowers, vigorous growth, and extended period of bloom.

* * * * *

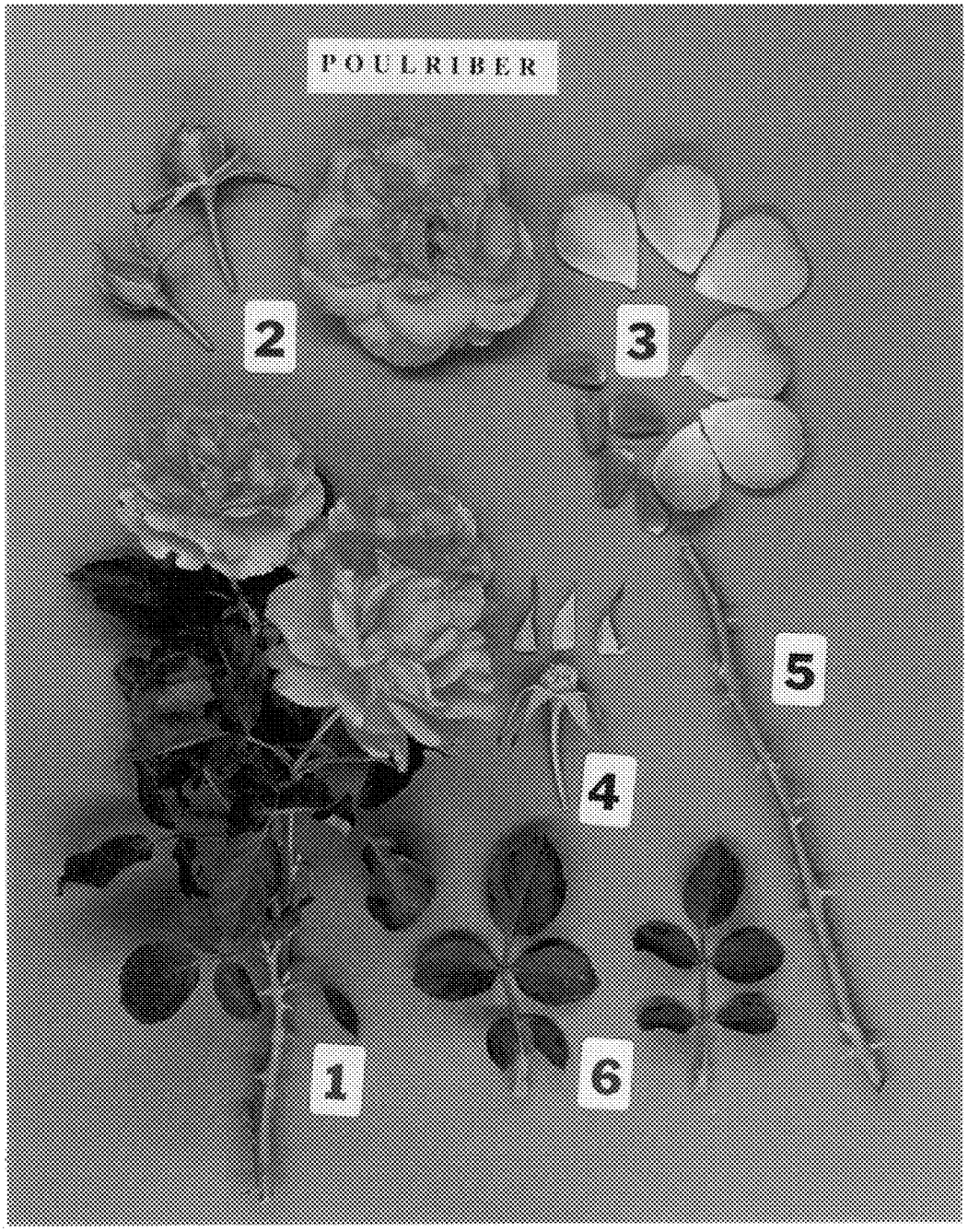
POULRIBER
2
3
5
4
1
6